(12) United States Patent
Petzoldt (10) Patent No.: US 8,851,100 B2
(45) Date of Patent: Oct. 7, 2014

(54) SAMPLING AND REJECTION DEVICE (75) Inventor: Kevin Petzoldt, St. Louis, MO (US)

(73) Assignee: Automation Tech, Inc., Perryville, MO (US)

( * ) Notice: Subject to any disclaimer, the term of this patent is extended or adjusted under 35 U.S.C. 154(b) by 271 days.

(21) Appl. No.: 13/016,284

(22) Filed: Jan. 28, 2011

(65) Prior Publication Data

US 2012/0192949 A1 Aug. 2, 2012

(51) Int. Cl.
| | |
|---|---|
| G05D 11/00 | (2006.01) |
| G01N 1/10 | (2006.01) |
| F01K 9/00 | (2006.01) |
| F16T 1/48 | (2006.01) |
| G01N 1/40 | (2006.01) |

(52) U.S. Cl.
CPC .......... *G01N 1/10* (2013.01); *G01N 2001/4033* (2013.01); *F01K 9/00* (2013.01); *F16T 1/48* (2013.01); *G01N 2001/105* (2013.01)
USPC .......... 137/88; 137/5; 137/115.01; 137/87.06

(58) Field of Classification Search
USPC ............. 137/5, 115.01, 118.01, 119.1, 87.05, 137/87.06, 93
See application file for complete search history.

(56) References Cited

U.S. PATENT DOCUMENTS

| | | | |
|---|---|---|---|
| 3,586,294 A | * | 6/1971 | Strong ........................ 366/163.2 |
| 3,743,598 A | * | 7/1973 | Field ............................ 210/709 |
| 3,824,372 A | | 7/1974 | Eaton |
| 3,905,385 A | | 9/1975 | Green |
| 3,950,137 A | | 4/1976 | Larson et al. |
| 3,955,403 A | | 5/1976 | Bodmer |
| 4,308,889 A | | 1/1982 | Lin et al. |
| 4,453,499 A | | 6/1984 | Palmer |
| 4,464,315 A | | 8/1984 | O'Leary |
| 4,639,718 A | | 1/1987 | Gasper |
| 4,822,744 A | | 4/1989 | Bellows |
| 4,830,757 A | | 5/1989 | Lynch et al. |
| 4,833,622 A | | 5/1989 | Barto et al. |

(Continued)

FOREIGN PATENT DOCUMENTS

| | | |
|---|---|---|
| JP | 2008121942 A2 | 5/2008 |
| KR | 2007721 A | 1/2002 |
| KR | 9019045 A | 2/2009 |

OTHER PUBLICATIONS http://www.merriam-webster.com/dictionary/tank. Aug. 2013.*

(Continued)

*Primary Examiner* — Stephen M Hepperle
*Assistant Examiner* — R. K. Arundale
(74) *Attorney, Agent, or Firm* — Polsinelli PC (57) ABSTRACT

A sampling and rejection device for a boiler or steam generating system is described. The sampling and rejection device receives the condensate or fluid and allows a volume of the condensate to liquefy or the fluid to build up in the interior of the sampling and rejection device. One or more conductivity, pH, and temperature sensors or probes are positioned in the sampling and rejection device to measure the condensate. The sampling and rejection device includes a collection vessel to hold and temporarily store the condensate. The sampling and rejection device includes an outlet or a return line (to a central boiler) and a drain line. If the sensor measures undesirable conductivity, pH, or temperature in the condensate in the collection vessel, then a valve to the drain line is opened and the condensate is rejected.

23 Claims, 5 Drawing Sheets

(56) References Cited

U.S. PATENT DOCUMENTS

| | | | |
|---|---|---|---|
| 4,905,721 | A | 3/1990 | Muccitelli |
| 5,448,178 | A | 9/1995 | Chen et al. |
| 5,747,342 | A | 5/1998 | Zupanovich |
| 6,196,253 | B1 | 3/2001 | Love |
| 6,279,593 | B1 | 8/2001 | Sheppard |
| 6,331,207 | B1 | 12/2001 | Gebhardt |
| 6,336,058 | B1 | 1/2002 | Fowee |
| 6,418,958 | B1 | 7/2002 | Rossi et al. |
| 6,622,745 | B1 * | 9/2003 | Smith et al. ............ 137/2 |
| 7,208,117 | B2 | 4/2007 | Hays et al. |
| 7,311,115 | B1 * | 12/2007 | Wendell et al. ........ 137/119.1 |
| 8,068,033 | B2 * | 11/2011 | Blokker et al. ............ 340/603 |
| 8,130,106 | B1 * | 3/2012 | Hicks et al. ............ 340/603 |
| 2008/0151684 | A1 * | 6/2008 | Lamon ............ 366/173.1 |
| 2010/0109885 | A1 | 5/2010 | Blokker et al. |

OTHER PUBLICATIONS

"Nozzle", American Heritage Dictionary, Mar. 2014.*

DL421/422 DirectLine® Sensor for Durafet® II and Meredian® II pH/ORP Electrodes Specification, Honeywell, Industrial Measurement and Control, 2003 (8 pages).

Industrial Electrolytic Conductivity Cells for UDA2182 Series, DirectLine® Modules and APT Series Specification, Honeywell, Industrial Measurement and Control, 2006 (8 pages).

DL423 DirectLine® Sensor Module for Conductivity Measurement Specification, Honeywell, Industrial Measurement and Control, 2003 (8 pages).

7774 pH/ORP Electrode Insertion/ Removal Assemblies Specification, Honeywell, Industrial Automation and Control, 1996 (4 pages).

* cited by examiner

SAMPLING AND REJECTION DEVICE

FIELD OF INVENTION

The present invention relates to a sampling and rejection device that monitors conductivity, pH, temperature, or other physical/chemical characteristics of condensate in a steam generating or boiler system.

BACKGROUND INVENTION

Boilers and stream generating systems are commonly used in industrial, institutional, and power generating facilities. One or more steam generators, such as, for example, a boiler, heat water or fluid to form steam, which is distributed throughout the facility to provide steam for use in comfort, process, or power generation applications. The condensate or condensed steam is returned to the boiler or the steam generator for efficiency.

The boilers and steam generating system are designed to operate with condensate having conductivity, pH, and temperature within targeted ranges. When the conductivity, pH, and temperature of the condensate deviates out of the targeted range, problems in the condensate of a steam generating system may develop. These problems may include mineral scale, carbonic corrosion, and thermal fatigue. These problems may result in costly maintenance and repairs to the steam generating systems.

Conditioning chemicals or amines are commonly used to treat the condensate in the steam generating systems. The conditioning chemicals are designed to minimize the corrosion caused by carbonic acid.

Heat exchangers are utilized in many steam generating systems. Problematic or defective heat exchangers can result in condensate contamination and temperature losses.

In general, quality condensate is considered to be low in conductivity, low in hardness, alkaline with respect to pH, heated, and essentially distilled water.

SUMMARY OF INVENTION

A sampling and rejection device for a steam generating system is described. The sampling and rejection device receives the condensate or fluid and allows a volume of the condensate to liquefy and build up in an interior of the sampling and rejection device. One or more sensors or probes are mounted in the sampling and rejection device to measure physical or chemical characteristics of the condensate, such as conductivity, pH, and/or temperature. The sampling and rejection device includes a collection vessel to hold and temporarily store the condensate. The sampling and rejection device includes an outlet or a return line (to the steam generator) and a drain line. If one of the sensors measures the condensate out of acceptable parameters or targeted ranges in the collection vessel, then a valve to the drain line is opened and the undesirable condensate is removed from the sampling and rejection vessel. Otherwise, the return line or the outlet passes the condensate back to the steam generator. An alarm and/or data logging equipment may be in electrical communication with the sensor to record the time/date when the event occurred.

In one aspect, a sampling and rejection device for condensate from a steam generating system is described. The sampling and rejection device includes a collection vessel defining an interior to hold a volume of condensate; an inlet in fluidic communication with the interior of the collection vessel to pass condensate to the interior; an outlet in fluidic communication with the interior of the collection vessel; a rejection outlet in fluidic communication with the interior of the collection vessel, the rejection outlet comprising a dump valve to control flow of condensate through the rejection outlet; one or more sampling probes, such as a conductivity sampling probe to measure the conductivity of the condensate in the interior of the collection vessel, a pH sampling probe to measure the acidity versus alkalinity of the condensate, and/or a temperature probe to measure liquid temperature of the condensate; and, a controller in electrical communication with the dump valve and the one or more sampling probes, wherein the controller opens the dump or reject valve based on readings from the sampling probes.

In another aspect, a method of monitoring a fluid in a steam generating system is described. The method includes providing a sampling and rejection device, the device comprising a collection vessel defining an interior; an inlet in fluidic communication with the interior of the collection vessel; an outlet in fluidic communication with the interior of the collection vessel; a rejection outlet in fluidic communication with the interior of the collection vessel, the rejection outlet comprising a dump valve to control flow of fluid through the rejection outlet; one or more sampling probes, such as a conductivity sampling probe to measure the conductivity of the fluid in the interior of the collection vessel, a pH probe to measure the acidity and alkalinity of the condensate, or a temperature probe to measure the temperature of the condensed steam; and, a controller in electrical communication with the probes. The method includes opening the dump valve if a conductivity level exceeds a threshold level or if pH and temperature are not in their targeted range.

In another aspect, a steam generator system is described. The steam generator system includes a central boiler for generating steam; pipes or lines to distribute the steam about an industrial facility; a sampling and rejection device positioned in the boiler system, the device comprising: a collection vessel defining an interior; an inlet in fluidic communication with the interior of the collection vessel; an outlet in fluidic communication with the interior of the collection vessel; a rejection outlet in fluidic communication with the interior of the collection vessel, the rejection outlet comprising a dump valve to control flow of fluid through the rejection outlet; one or more sampling probes, such as a conductivity sampling probe to measure the conductivity of the fluid in the interior of the collection vessel, a pH probe to measure the acidity and alkalinity of the condensate, or a temperature probe to measure the temperature of the condensed steam; and, a controller in electrical communication with the dump valve and the sampling probes, wherein the controller opens the dump valve based on the readings from the sampling probes.

In another aspect, a sampling and rejection device for condensate from a boiler or steam generating system is described. The device includes a tank to receive a volume of condensate. An inlet is in fluidic communication with an interior of the tank to pass the condensate to the interior. An outlet is in fluidic communication with the interior of the tank. An output line is in fluidic communication with the outlet. One or more valves selectively control fluid flow from the output line to a condensate return line and a waste water line. One or more sampling probes measure physical or chemical characteristics of the condensate in the interior of the tank. A controller is in electrical communication with the one or more valves and the one or more sampling probes. The controller opens and closes the one or more valves based on the readings from the one or more sampling probes to direct fluid to the condensate return line or the waste water line.

DETAILED DESCRIPTION OF INVENTION

Figure 1:
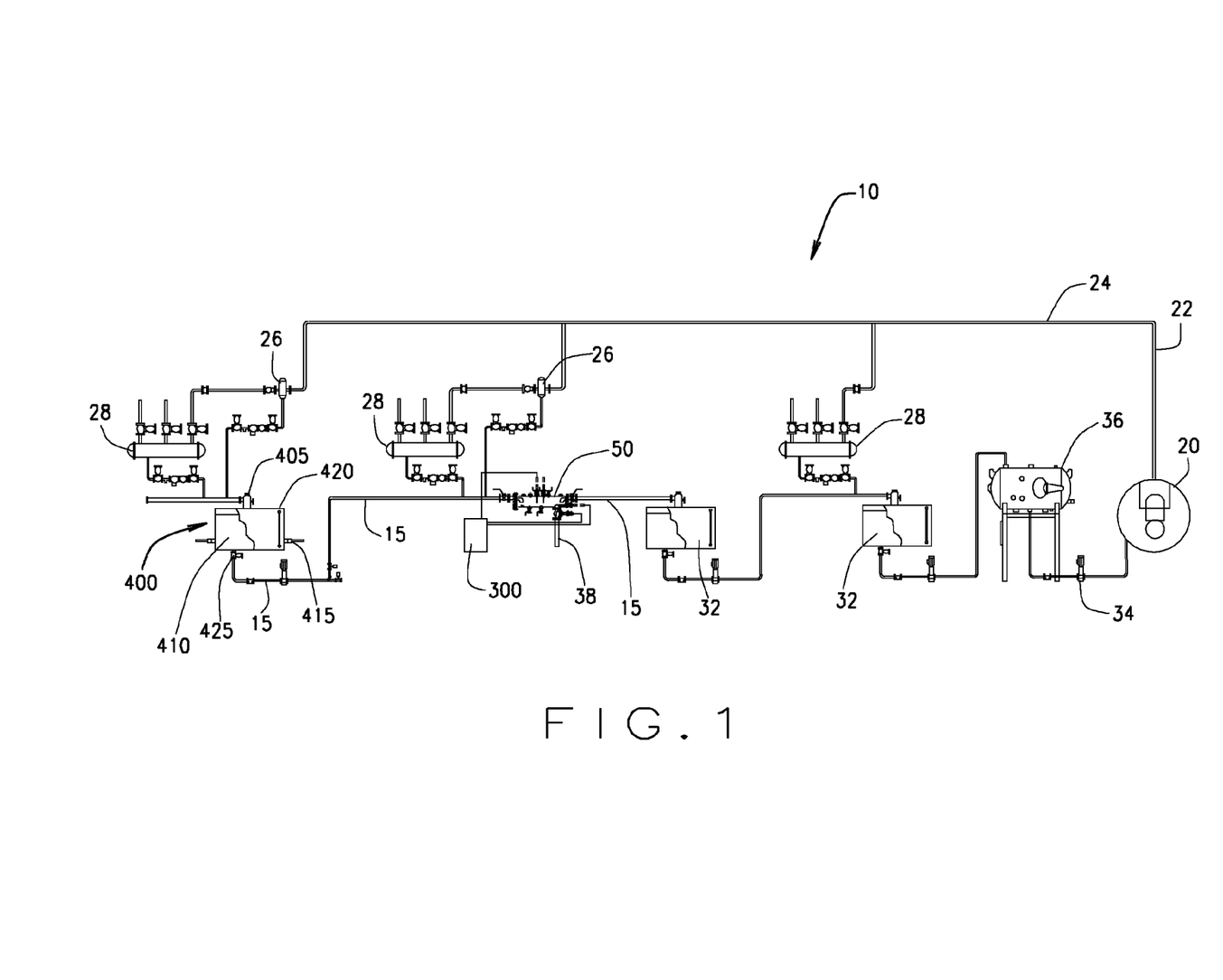
FIG. 1 is a schematic diagram of the boiler system.

The sampling and rejection device will now be described with reference to the FIGS. With reference to FIG. 1, a sampling and rejection device 50 is typically positioned in a condensate return line 15 of a boiler system 10. As such, the sampling and rejection device 50 samples the condensate before the condensate returns to a central boiler 20 of the boiler system 10. One or more sampling and rejection devices 50 may be positioned throughout the boiler system 10. The sampling and rejection device 50 may be installed or retrofitted in to existing boiler systems 10 or included in new boiler systems 10.

Generally, the boiler system 10 forms a loop through out the industrial facility. The central boiler 20 heats water provided to or condensate returned to the central boiler 20 to form the steam. The steam is distributed throughout the industrial facility. The steam may cool and form liquid condensate as it travels through the industrial facility. And, the condensed steam or "condensate" is returned for efficiency. As such, the condensate returned to the boiler feed-water or make-up vessel is susceptible to contamination. Constantly adding fresh water to the boiler system 10 is expensive and not desirable as fresh water (make-up water) should be chemically pre-treated, heated, and chemically treated.

The boiler system 10 includes the central boiler 20, which is in fluidic communication via pipes, lines, conduits, etc. with heating apparatus, heat exchangers, processing equipment, etc. throughout the industrial facility that require or use the steam from the central boiler 20. The central boiler 20 heats water to form steam, which is then distributed by the steam lines. The steam reaches its destination and is injected, utilized in a heat exchanger, trapped in a steam trap, and then returned to the central boiler 20 via the condensate return line 15.

The boiler system 10 will be described with reference to FIG. 1. From the central boiler 20, the steam passes to a steam header 22, which is in fluid communication with the remainder of the boiler system 10, including steams lines 24, which pass the steam to the various applications for use. From the applications, the returning steam may pass through dryers 26 and accumulators 28 to collect the condensate. The condensate may then pass via the condensate return line 15 to the sampling and rejection device 50 for processing and/or monitoring. The "good or desirable" condensate, i.e., the condensate with conductivity, pH, and/or temperature within a targeted range or below threshold levels, may pass to a make up water tank 32, which is fluidic communication with the central boiler 20 by a transfer pump 34. The make up water tank 32 may also be in supply communication with a municipal water supply to additional water to the boiler system 10 as additional water is demanded to maintain adequate fluid levels in the boiler system 10. The central boiler 20 may include a main tank 36 for storage of fluid for immediate use in the central boiler 20. The "bad or undesirable condensate" passes to a waste water line 38 for disposal.

Conductivity less than 50 umohs is typically considered to be acceptable or desirable. Desirable pH and temperature of the condensate is based and dependent on the system engineering and type of chemical treatment being used. For example, in some systems, the condensate should have a temperature reading of greater than approximately 160°-180° F., and the condensate should have a neutral to alkaline pH. In other systems, these values may vary.

Failure of the boiler system 10 may lead to lost productivity or closing of the facility. Replacing or fixing the central boiler 20 may prove costly.

Typically, the sampling and rejection device 50 is positioned remote from the central boiler 20. The condensate return line 15 fluidly connects the sampling and rejection device 50 with the central boiler 20.

The sampling and rejection device 50 may be several hundred feet or more from the central boiler 20. The use of multiple sampling and rejection devices 50 assists in determining a specific location or point in the boiler system 10 that is causing the undesirable condensate. With multiple sampling and rejection devices 50 positioned in different locations or points throughout the industrial facility, it may be easier to locate or pinpoint the cause of an undesirable conductivity, pH, or temperature reading. This may assist in efficiently performing the necessary repairs to the boiler system 10.

Figure 2:
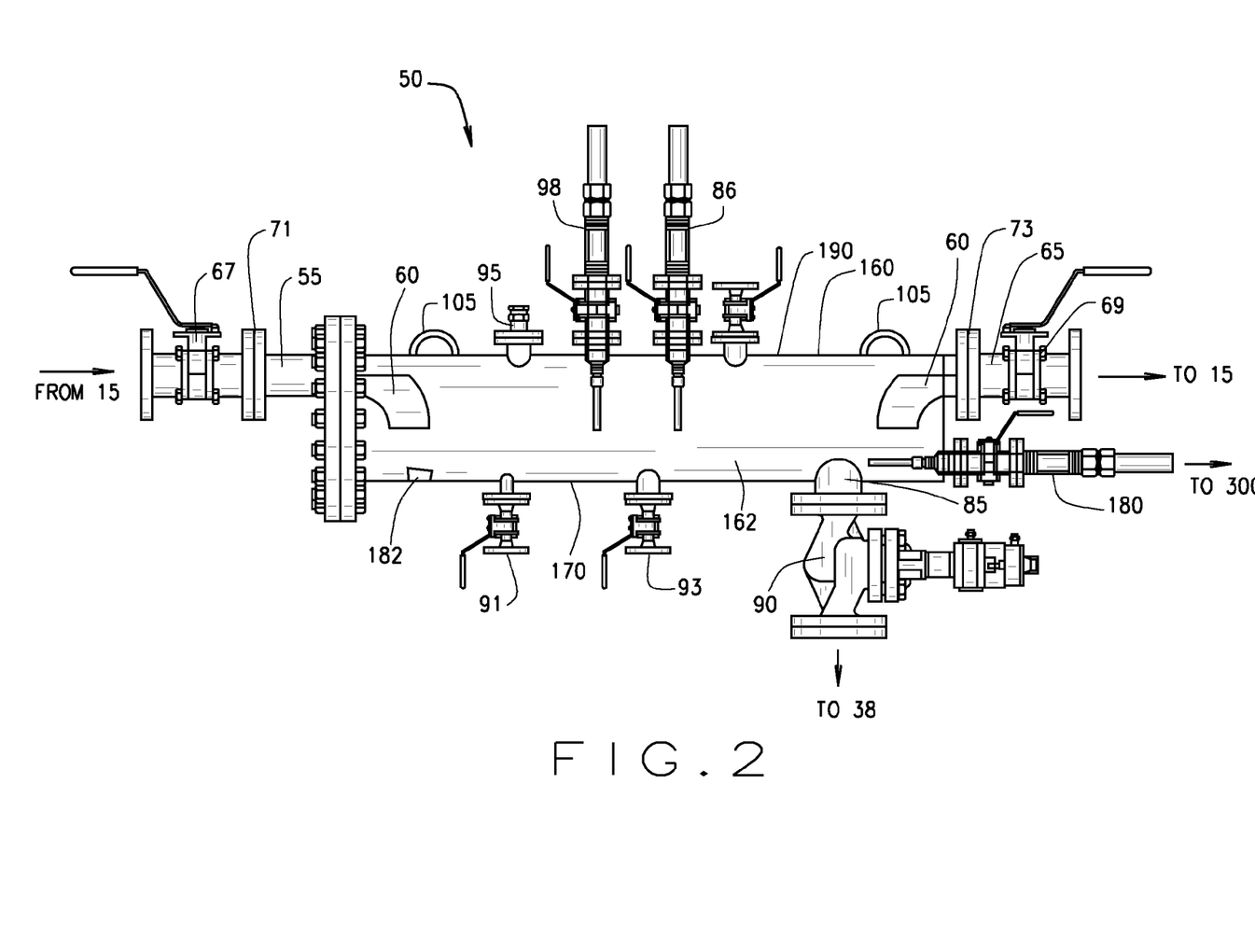
FIG. 2 is a side sectional view of the sampling and rejection device.
Figure 3A:
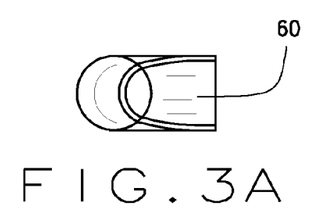
FIGS. 3(A)-(G) are views of the input nozzle.
Figure 3B:
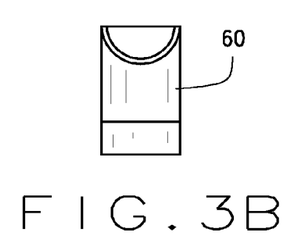
Figure 3C:
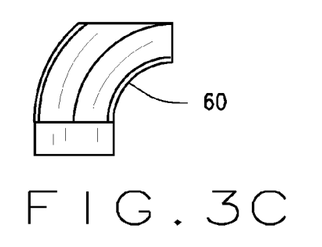
Figure 3D:
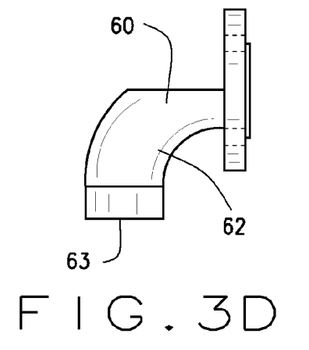
Figure 3E:
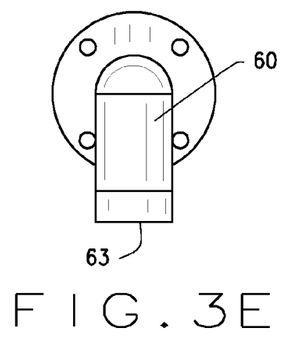
Figure 3F:
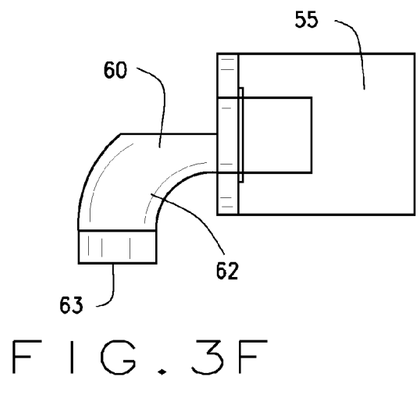
Figure 3G:
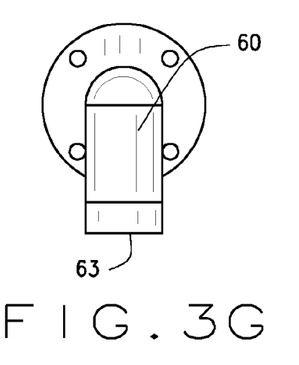

The sampling and rejection device 50 includes a collection vessel 160 to receive the condensate. The collection vessel 160 includes an interior volume 162 to contain a quantity of the condensate. The collection vessel 160 may include a tank or other liquid receptacle. The collection vessel 160 may be made from stainless steel or other non-reactive material. The interior volume 162 of the collection vessel 160 is generally hollow to hold the condensate.

The sampling and rejection device 50 includes an inlet 55 in fluidic communication with the interior of the collection vessel 160. The inlet 55 provides for condensate to enter into the interior volume 162 of the collection vessel 160. The inlet 55 is in fluidic communication with the condensate return line 15 of the boiler system 10.

An outlet 65 is in fluidic communication with the interior volume 162 of the collection vessel 160. The outlet 65 passes the condensate back to the central boiler 20 or the make-up tank 32 in fluidic communication with the central boiler 20 via the condensate return line 15. A rejection outlet 85 is in fluidic communication with the interior of the collection vessel 160 and is for condensate that should not pass back to the central boiler 20. The rejection outlet 85 passes the condensate to the waste water line 38.

Typically, the outlet 65 and the inlet 55 are positioned on opposite sides of the sampling and rejection device 50 in order to allow the condensate to mix and circulate with the volume of condensate in the collection vessel 160. The outlet 65 and the inlet 55 are further positioned above a bottom floor 170 of the collection vessel 160 in order to allow the volume of the condensate to build up in the collection vessel 160 before the condensate passes through the outlet 65. By positioning the outlet 65 above or a distance from the bottom floor, the condensate must reach a certain depth or volume in the collection vessel 160 before there will be sufficient condensate such that the condensate may exit the collection vessel 160 via the outlet 65. Further, a conductivity probe 180, a pH probe 98, and/or a temperature probe 86 are positioned or spaced a distance from the bottom floor 170 of the sampling and rejection device 50. This increases the sample size of the condensate that is be tested by the conductivity probe 180, the pH probe 98, and the temperature probe 86. This provides for more accurate readings of the physical and chemical characteristics of the condensate. By allowing a volume of at least approximately 1 gallon to approximately 40 gallons of condensate to build in the collection vessel 160, the conductivity probe 180, the pH probe 98, and/or the temperature probe 86 are flooded or submersed with the condensate. Although the conductivity probe 180, the pH probe 98, and the temperature probe 86 are described, the device 50 may include one of said probes, combinations of any of two of said probes, all three of said probes, or additional probes to measure or monitor other physical and chemical characteristics of the condensate.

The rejection outlet 85 is typically positioned in the bottom floor 170 to allow the condensate to drain from the collection vessel 160.

The inlet 55 and/or the outlet 65 may also include structures that point or orient toward the bottom floor 170 of the collection vessel 160. Such an orientation encourages the condensate to mix in the collection vessel 160 before the condensate exits the collection vessel 160 via the outlet 65. Further, the inlet 55 and/or the outlet 65 may include a widening portion to prevent back-pressure from forming in the collection vessel 160.

For example, the inlet 55 includes nozzle 60, which expands in diameter and points toward the bottom floor 170 of the collection vessel 160. The nozzle 60 has an increased diameter 62 compared to the inlet 55. The nozzle 60 may include a 90° elbow that passes into the interior of the collection vessel 160. An outlet 63 of the nozzle 60 points toward the bottom floor 170.

The inlet 55 and the outlet 65 may optionally include valves 67, 69 which open or close the sampling and rejection device 50. The valves 67, 69 may include ball valves. Such may be useful in bypassing the sampling and rejection device 50.

The sampling and rejection device 50 may be plumbed in the condensate return line 15 via flange connections, welding, soldering, and the like. FIG. 2 shows flanging connections 71, 73 that fluidly connect the device 50 to the boiler system 10.

The sampling and rejection device 50 may further include one or more drain valves 91, 93. The drain valves 91, 93 maybe used by the operator to manually drain the sampling and rejection device 50. The drain valves 91, 93 may include ball valves.

The sampling and rejection device 50 may include a vacuum break 95 in order to prevent a vacuum from forming in the sampling and rejection device 50. The vacuum break prevents vacuums from forming to due to fluctuations in temperature of the condensate or liquids in the boiler system 10.

The sampling and rejection device 50 may include a pressure relief in order to prevent or reduce damage from a system 10 that fails and builds up pressure in the sampling and rejection device 50.

The sampling and rejection device 50 may further include one or more attachment devices 105, such as, for example, hooks, loops, openings, or other connectors that are integral or attached to the top portion 190 of the sampling and rejection device 50. The attachment devices 105 assist in positioning the sampling and rejection device 50 within the boiler system 10. The attachment devices 105 may assist in suspending or holding the device 50.

The condensate feeds to the sampling and rejection device 50 via gravity. The collection vessel 160 is vented. The collection vessel 160 may include a vent on a top portion 190 of the collection vessel 160.

The rejection outlet 85 includes a dump valve 90 to allow the device 50 to dump the fluid in the device 50 when the conductivity, pH, and/or temperature exceeds certain threshold or targeted levels. The rejection outlet 85 is in fluidic communication with a sewer or other wastewater holding tank. By dumping the fluid through the rejection outlet 85, fluid with high levels of conductivity, unacceptable pH, or unacceptable temperature levels are not returned to the central boiler 20.

The sampling and rejection device 50 may further include a fluid level sensor 182 to measure the fluid level in the collection vessel 160.

Figure 4:
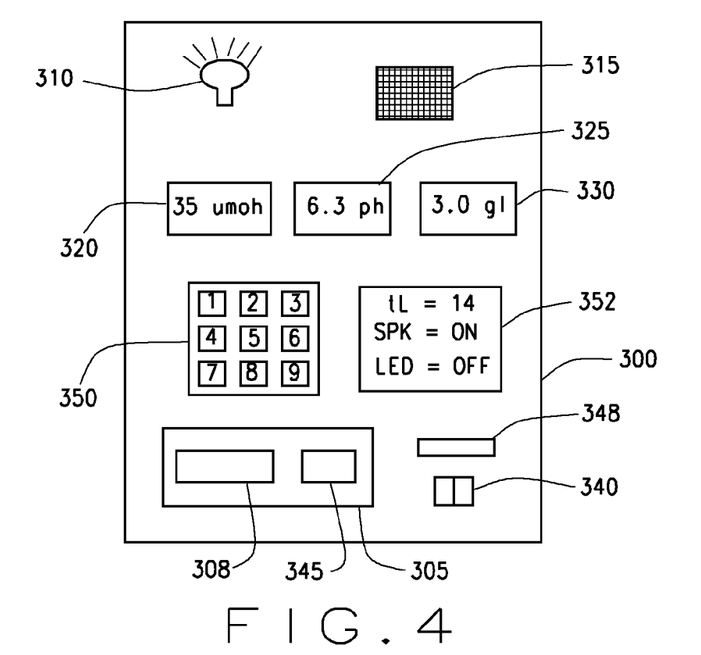
FIG. 4 is a plan diagram of the controller.

The controller 300 may include a microprocessor, logic controller, circuit board, NEMA 4 Panel, or other control panels. The controller 300 includes input devices for the operator to program the threshold levels or the targeted ranges of conductivity, pH, and temperature that cause the dump valve 90 to open and close. The controller 300 may be programmed to set different threshold levels of conductivity, pH, and temperature that cause the controller 300 to open the dump valve 90.

The controller 300 may be programmed to where the dump valve 90 opens upon measuring conductivity exceeding 50 umohs, undesirable pH levels, and/or undesirable temperature levels. Of course, the controller 300 may be programmed to open the dump valve 90 at higher or lower conductivity, pH, and temperature levels depending upon the settings programmed by the operator.

The controller 300 may also maintain the dump valve 90 in an open position for a predetermined amount of time upon a signal to open the dump valve 90. For example, after the probe measures a conductivity level above the threshold level, the controller 300 may maintain the dump valve 90 in the open position for 10 minutes or other time period defined or inputted by the operator. The time period may allow the collection vessel 160 to drain through the rejection outlet 85.

The controller 300 may also maintain the dump valve 90 in an open position until the conductivity levels drop below a closing threshold. For example, the dump valve is maintained in the open position until the conductivity level is below 50 umohs or other level defined or inputted by the operator. This closing threshold may be the same or different than the threshold that caused the dump valve 90 to open. When the conductively level falls below the threshold, or the pH and/or temperature is desirable, the controller 300 will close the dump valve 90 and the collection vessel 160 will fill until the fluid is a sufficient level to again exit through the outlet 65 and to the condensate return line 15.

The controller 300 may also maintain the dump valve 90 in an open position until an operator manually resets the controller 300 and the dump valve 90 back to the closed position. As such, the dump valve 90 continues to dump the condensate until the operator closes the dump valve 90.

The controller 300 may also be programmed to where the dump valve 90 opens when the conductivity measures in or over a particular range of conductivity, pH, or temperature over a particular time period. As such, the dump valve 90 opens when an average conductivity, pH, temperature for a time period is out of a targeted range. For example, the dump valve 90 may open when the conductivity measures above 50 umohs for a period of one minute. In this example, such programming would prevent dumping of the condensate for momentary spikes in the conductivity levels.

The controller 300 may also include alarm modules, modes, or processes that signal an audible, visual (LED for example), or other notification action that the conductively, pH, or temperature levels have exceeded the threshold level.

The notification action may include an electronic mail message, text message, telephone message, or other communication. Such alarms notify the operator of a conductivity, pH, or temperature level exceeding the threshold level or out of the target range.

The controller 300 may also include a data logging module 305 that records or saves relevant information regarding the event. The data logging module 305 may save or record data and information, such as, the time, date, conductivity levels, pH levels, temperature levels, flow rates of condensate, levels of condensate in the collection vessel 160, etc. The data logging module 305 may include flash download for transfer of the data to a computing system or other device. The controller 300 may include an Ethernet port 340 for downloading data from the controller 300. The data logging module 305 may include a sub-controller 308 for processing the data and information for the data logging functions.

An example of the controller 300 in shown in FIG. 4. The controller 300 includes a visual alarm 310 to provide a visual alert when the conductivity levels, pH levels, temperature levels are in excess of the threshold level or out of the targeted range. The controller includes a speaker 315 to provide an audible alert when the conductivity levels, pH levels, or temperature levels are in excess of the threshold level. The controller 300 includes first visual and second visual displays 320 and 325 to show the current conductivity levels, pH, temperature, or other characteristics of the condensate. The visual displays 320 and 325 are in electrical communication with the conductivity probe 180, the pH probe 98, and the temperature probe 86. The controller 300 may include a third visual display 330 to show the current fluid levels in the collection vessel 160, if the optional fluid level sensor 182 is employed. The controller 300 may include the Ethernet port 340 in order to access an internal memory 345 of the data logging module 305. The controller 300 may include a memory card port 348 if removable memory devices are employed. The controller 300 further may further include an interface 350 for the operator to adjust and program the controller 300 regarding the threshold level, the closing threshold level, the targeted ranges for temperature, pH and conductivity, and other user defined variables herein described. The interface 350 may include a touch screen, keys, knobs, or other suitable controls. The interface 350 may include a screen display 352.

The controller 300 may be integral to the sampling and rejection device 50, positioned proximate to the sampling and rejection device 50, positioned or integrated with or into the central boiler 20, or positioned in a control room. The controller 300 may be in direct wired electrical communication with the conductivity probe 180, the temperature probe 86, the dump valve 90, the pH sensor 98, an optional level sensor 182, and other electrical components of the sampling and rejection device 50. The controller 300 may also be in wireless electrical communication with the conductivity probe 180, the temperature probe 86, the dump valve 90, the pH probe 98, an optional level sensor 182, and other electrical components of the sampling and rejection device 50.

The sampling and rejection device 50 may be formed from an approximately round length of pipe. Although a round pipe is described, the sampling and rejection device 50 may include other shapes that hold a quantity of the condensate. For example, the sampling and rejection device 50 may include a rectangular, round, ovular, etc. shaped collection vessel 160. The sampling and rejection device 50 may also include a standard tank or bucket shaped receptacle.

The pipe may have a diameter of approximately 8 to approximately 24 inches and length of approximately 2 feet to approximately 10 feet. The length and width of the sampling and rejection device 50 will depend upon the specific application of the sampling and rejection device 50. The sampling and rejection device 50 may be scaled up or down depending upon the particular application of the sampling and rejection device 50 and the quantity of condensate passing through the sampling and rejection device 50.

The sampling and rejection device 50 is in electrical communication with the controller 300. The controller 300 is in electrical communication with the conductivity probe 180, the temperature probe 86, the dump valve 90, the pH probe 88, the optional level sensor 182, and other electrical components of the sampling and rejection device 50.

The conductivity probe 180 may include probes or other conductivity measuring apparatus to the measure the conductivity of a solution. Such probes are commercially available from Honeywell as Models DL421/422/423 Direct Line® Sensors.

Figure 5:
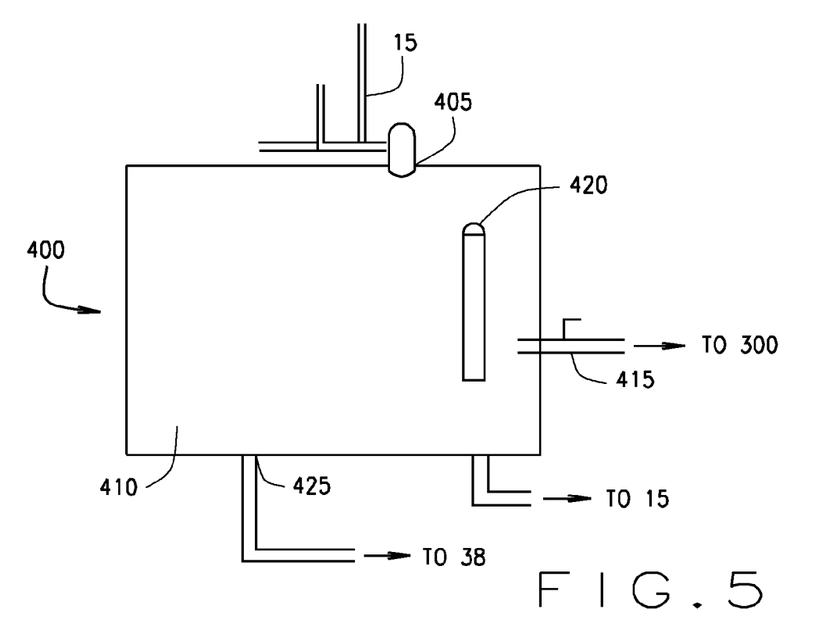
FIG. 5 is a side sectional view of the second sampling and rejection device.

A second sampling and rejection device 400 is shown in FIG. 5. The sampling and rejection device 400 operates similarly to the sampling and rejection device 50. An inlet 405 in a top portion of a tank 410 provides condensate to the tank 410 from the condensate return line 15. A conductivity probe 415 measures conductivity of the condensate. The conductivity probe 415 is in electrical communication with a processor, such as the controller 300. An outlet 420 provides an exit for the condensate. The outlet 420 is positioned above a bottom of the tank 410. A rejection outlet 425 drains the tank 410 when conductivity levels are elevated.

Figure 6:
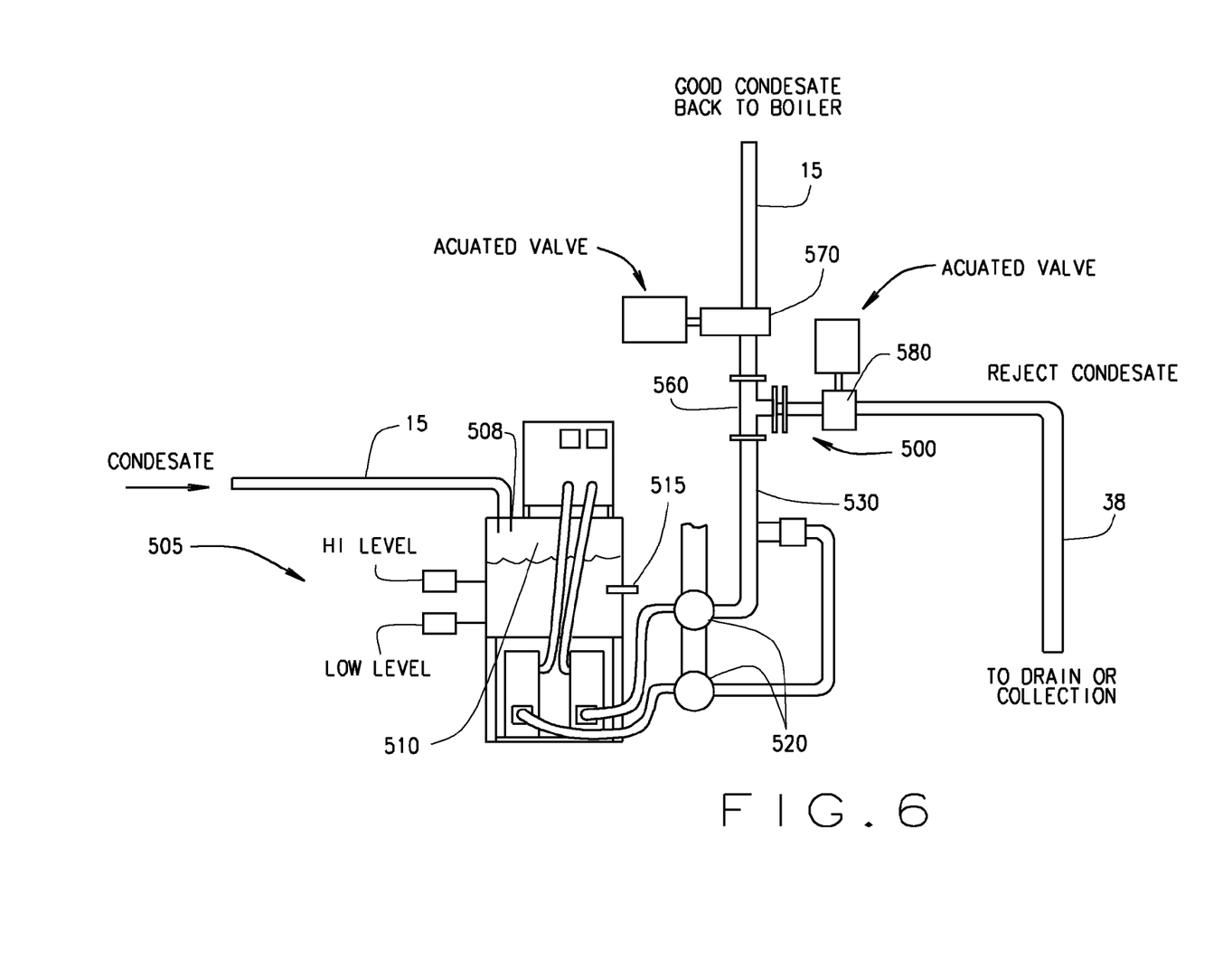
FIG. 6 is a side sectional view of the third sampling and rejection device.

A third sampling and rejection device 500 is shown in FIG. 6. The device 500 may be used in conjunction with the pumps of a lift station or condensate receiver. The sampling and rejection device 500 operates similarly to the sampling and rejection device 50. As shown in FIG. 6, a condensate receiver 505, such as a Series CBE Condensate Return Unit, commercially available from ITT Domestic Pump, is used with the device 500. An inlet 508 in a top portion of the condensate receiver 505 provides condensate to a tank 510 from the condensate return line 15. A conductivity probe 515 is inserted into or positioned in the tank 510 to contact the condensate. The conductivity probe 515 measures the conductivity of the condensate in the tank 510. The conductivity probe 515 is in electrical communication with a processor, such as the controller 300.

When the level of condensate in the tank 510 reaches an upper level, the condensate receiver 505 will cycle one or more pumps 520 to cause flow from the condensate receiver 505 to an output line 530 that is in fluidic communication with the condensate return line 15. The output line 530 includes a flow control or diverter to either allow the condensate to pass to the condensate return line 15 or to the waste water line 38, depending upon the conductivity levels measured by the conductivity probe 515.

The flow control may include a first valve 570 and a second valve 580 that are in the output line 530. For example, a splitter or T connection 560 may be joined to or positioned in the output line 530 in order to split or branch the output line 530 into lines leading to the condensate return line 15 and to the waste water line 38. The controller 300 opens and closes the valves 570, 580 in order to prevent condensate with high conductivity from reaching the central boiler 20. The first valve 570 opens and closes flow to the condensate return line 15, while the second valve 580 opens and closes flow to the waste water line 38. Both the first and the second valves 570, 580 are in electrical communication with the controller 300 or other suitable logic controller configured to actuate the valves 570, 580. The first valve 570 allows good condensate to return to the central boiler 20, while the second valve 580 rejects the condensate to the waste water line 38, drain, collection tank, or other area away from the central boiler 20. If the conductivity of the sampled condensate is within the targeted ranges or below the threshold level programmed into the controller 300, the first valve 570 will open or remain open and the second valve 580 will close or remain closed. When the sampled condensate is out of the targeted range or exceeds the threshold level, the controller 300 will close the first valve 570 and open the second valve 580 to prevent such condensate from reaching the central boiler 20.

Similar to the other embodiments described herein, the controller 300 may toggle the valves 570, 580 as necessitated by the conductivity levels measured by the conductivity probe 515. The controller 300 opens and closes the one or more valves 570, 580 based on the readings from the conductivity probe 515 to direct fluid to the condensate return line 15 or the waste water line 38.

An existing boiler system 10 may be modified or retrofitted to include the sampling and rejection device 500. For example, the condensate receiver 505 may be fitted with the conductivity probe 515 by inserting the conductivity probe 515 through a sidewall of the tank 510. The T connection 560 may be plumbed into the existing condensate return line 15, and hosing may be added to drain the rejected condensate from the second valve 580.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

What is claimed:

1. A sampling and rejection device for condensate from a boiler steam generating system, comprising:
    a collection vessel defining an interior to hold a volume of condensate; the collection vessel comprising a bottom floor;
    an inlet in fluidic communication with the interior of the collection vessel to pass condensate to the interior, the inlet comprising an inlet nozzle;
    an outlet in fluidic communication with the interior of the collection vessel, the outlet comprising an outlet nozzle;
    a rejection outlet in fluidic communication with the interior of the collection vessel, the rejection outlet comprising a dump valve to control flow of condensate through the rejection outlet, and wherein the rejection outlet is positioned in the bottom floor to allow the condensate to drain from the collection vessel;
    the inlet and the outlet are positioned above the bottom floor of the collection vessel to allow the volume of condensate to build up in the collection vessel;
    one or more sampling probes in the interior of the collection vessel to measure physical or chemical characteristics of the condensate in the interior of the collection vessel, wherein the one or more sampling probes are positioned or spaced a distance from the bottom floor of the collection vessel; and,
    a controller in electrical communication with the dump valve and the one or more sampling probes, wherein the controller opens the dump valve based on the readings from the one or more probes.

2. The sampling and rejection device according to claim 1, wherein the one or more sampling probes measure conductivity, pH, temperature, or combinations thereof, wherein the dump valve is programmed to dump the condensate in the device when the conductivity, pH, or temperature exceeds a threshold level or is out of a targeted range.

3. The sampling and rejection device according to claim 2, wherein the threshold level or the targeted range is set or changed by the operator.

4. The sampling and rejection device according to claim 2, wherein the device passes the condensate to the outlet so long as the conductivity, pH, and temperature levels do not exceed the threshold level or are within the targeted ranges.

5. The sampling and rejection device according to claim 2, wherein the controller maintains the dump valve in an open position until the conductivity, pH, or temperature levels fall below the threshold level or return to within the targeted range.

6. The sampling and rejection device according to claim 1, wherein the collection vessel includes an interior volume to contain a quantity of the condensate.

7. The sampling and rejection device according to claim 1, wherein the outlet and the inlet are positioned on opposite sides of the sampling and rejection device.

8. The sampling and rejection device according to claim 1, wherein the controller is programmed to open the dump valve when conductivity, pH, or temperature measures out of a targeted range or exceeds a threshold level over a time period.

9. The sampling and rejection device according to claim 1, wherein the controller maintains the dump valve in an open position until an operator manually resets the controller or the dump valve back to the closed position.

10. The sampling and rejection device according to claim 1, wherein the controller maintains the dump valve in an open position for a predetermined amount of time upon a signal to open the dump valve.

11. The sampling and rejection device according to claim 1, wherein the controller further comprises a data logging module.

12. The sampling and rejection device according to claim 1, wherein the controller further comprises an alarm module.

13. The sampling and rejection device according to claim 1, wherein the inlet nozzle points toward the bottom floor of the collection vessel.

14. The sampling and rejection device according to claim 1, wherein the inlet nozzle passes into the interior of the collection vessel.

15. The sampling and rejection device according to claim 1, wherein the collection vessel slows a flow of the condensate to collect the volume of condensate in the interior of the collection vessel.

16. The sampling and rejection device according to claim 15, wherein the collection vessel slows the condensate for sampling before passing the condensate to the outlet for return to the boiler steam generating system.

17. A method of monitoring a fluid in a boiler system, comprising:
    providing a sampling and rejection device, the device comprising a collection vessel defining an interior, the collection vessel comprising a bottom floor; an inlet in fluidic communication with the interior of the collection vessel, the inlet comprising an inlet nozzle; an outlet in fluidic communication with the interior of the collection vessel, the outlet comprising an outlet nozzle; the inlet and the outlet are positioned above the bottom floor of the collection vessel to allow a volume of condensate to build up in the collection vessel; a rejection outlet in fluidic communication with the interior of the collection vessel; the rejection outlet is positioned in the bottom floor to allow the condensate to drain from the collection vessel, the rejection outlet comprising a dump valve to control flow of fluid through the rejection outlet; one or more sampling probes to measure conductivity, pH, or temperature of the fluid in the interior of the collection vessel; wherein the one or more sampling probes are positioned or spaced a distance from the bottom floor of the collection vessel and, a controller in electrical communication with the dump valve and the one or more sampling probes, wherein the controller opens the dump valve based on conductivity, pH, or temperature readings from the one or more sampling probes;

passing the condensate to the sampling device of the collection vessel;

measuring the conductivity, pH, temperature, or combination thereof of the condensate; and opening the dump valve if the conductivity, pH, or temperature levels exceed a threshold level or are outside a target range.

18. The method according to claim 17, further comprising closing the dump valve after the conductivity, pH, or temperature level fall below the threshold level or returns to within the targeted range.

19. The method according to claim 17, further comprising adding make up water to a boiler system that incorporates the sampling and rejection device.

20. A boiler system, comprising:
a central boiler for generating steam;
pipes or lines to distribute the steam about an industrial facility;
a sampling and rejection device positioned in the boiler system, the device comprising:
   a collection vessel defining an interior to hold a volume of condensate; the collection vessel comprising a bottom floor;
   an inlet in fluidic communication with the interior of the collection vessel to pass the condensate to the interior, the inlet comprising an inlet nozzle;
   an outlet in fluidic communication with the interior of the collection vessel, the outlet comprising an outlet nozzle;
   the inlet and the outlet are positioned above the bottom floor of the collection vessel to allow the volume of condensate to build up in the collection vessel;
   a rejection outlet in fluidic communication with the interior of the collection vessel, the rejection outlet comprising a dump valve to control flow of fluid through the rejection outlet;
   one or more sampling probes to measure conductivity, pH, or temperature of the fluid in the interior of the collection vessel; wherein the one or more sampling probes are positioned or spaced a distance from the bottom floor of the collection vessel; and,
a controller in electrical communication with the dump valve and the one or more sampling probes, wherein the controller opens the dump valve based on readings from the one or more sampling probes.

21. The boiler system according to claim 20, wherein the sampling device is positioned remote from the central boiler.

22. The boiler system according to claim 20, wherein the boiler system comprises two or more sampling and rejection devices incorporated into the boiler system.

23. A boiler system, comprising:
a central boiler for generating steam;
pipes or lines to distribute the steam about an industrial facility;
a sampling and rejection device positioned in the boiler system, the device comprising a tank to receive a volume of condensate of approximately 1 gallon to approximately 40 gallons, the tank comprising a bottom floor;
an inlet in fluidic communication with an interior of the tank to pass the condensate to the interior, the inlet comprising an inlet nozzle;
an outlet in fluidic communication with the interior of the tank;
the inlet and the outlet are positioned above the bottom floor of the tank to allow the volume of condensate to build up in the tank;
an output line in fluidic communication with the outlet;
one or more valves to selectively control fluid flow from the output line to a condensate return line and a waste water line;
one or more sampling probes positioned above the bottom floor of the tank to measure physical or chemical characteristics of the condensate in the interior of the tank;
a controller in electrical communication with the one or more valves and the one or more sampling probes, wherein the controller opens and closes the one or more valves based on the readings from the one or more sampling probes to direct fluid to the condensate return line or the waste water line.

* * * * *